(12) United States Patent
Lee (10) Patent No.: US 8,864,727 B2
(45) Date of Patent: Oct. 21, 2014

(54) TRANSDERMAL DELIVERY SYSTEM, METHOD FOR MANUFACTURING THE SAME, AND TRANSDERMAL DELIVERY METHOD USING THE SYSTEM

(75) Inventor: Heonhan Lee, Jeonju-si (KR)

(73) Assignee: Samyang Biopharmaceuticals Corporation, Seoul (KR)

( * ) Notice: Subject to any disclaimer, the term of this patent is extended or adjusted under 35 U.S.C. 154(b) by 433 days.

(21) Appl. No.: 12/882,815

(22) Filed: Sep. 15, 2010

(65) Prior Publication Data

US 2011/0066120 A1 Mar. 17, 2011

Related U.S. Application Data

(60) Provisional application No. 61/242,854, filed on Sep. 16, 2009.

(30) Foreign Application Priority Data

Nov. 4, 2009 (KR) .......................... 10-2009-0106090

(51) Int. Cl.
- *A61F 13/02* (2006.01)
- *A61N 1/30* (2006.01)
- *A61M 35/00* (2006.01)
- *A61F 13/00* (2006.01)
- *A61K 9/70* (2006.01)

(52) U.S. Cl.
CPC .............. *A61F 13/02* (2013.01); *A61K 9/7061* (2013.01); *A61K 9/7092* (2013.01); *A61F 2013/00646* (2013.01)
USPC ............. 604/307; 604/19; 604/290; 604/304; 604/308

(58) Field of Classification Search
USPC .............. 424/443–449; 600/365; 604/307, 19
See application file for complete search history.

(56) References Cited

U.S. PATENT DOCUMENTS

| | | | |
|---|---|---|---|
| 4,911,916 A * | 3/1990 | Cleary .......................... | 424/449 |
| 5,006,342 A * | 4/1991 | Cleary et al. .................. | 424/445 |
| 5,310,559 A * | 5/1994 | Shah et al. ..................... | 424/448 |
| 5,538,736 A * | 7/1996 | Hoffmann et al. ............. | 424/448 |
| 6,791,003 B1 * | 9/2004 | Choi et al. ...................... | 602/48 |
| 2005/0048102 A1* | 3/2005 | Tapolsky et al. .............. | 424/448 |
| 2008/0254105 A1* | 10/2008 | Tapolsky et al. .............. | 424/447 |
| 2011/0190716 A1* | 8/2011 | Easterbrook et al. .......... | 604/307 |
| 2012/0078204 A1* | 3/2012 | Jackson et al. ................. | 604/290 |

(Continued)

FOREIGN PATENT DOCUMENTS

| KR | 10-2006-0025080 A | 3/2006 |
|---|---|---|
| KR | 10-2008-0006960 A | 1/2008 |
| KR | 10-2009-0009951 A | 1/2009 |

OTHER PUBLICATIONS

Chinese Patent Office, Chinese Office Action issued in corresponding CN Application No. 201080049146.5, dated Feb. 21, 2013.

(Continued)

*Primary Examiner* — Jason Flick
(74) *Attorney, Agent, or Firm* — Sughrue Mion, PLLC (57) ABSTRACT

Disclosed is a transdermal delivery system of multiple adhesive layers having a drug-free adhesive layer as an intermediate layer to control drug delivery rate. The transdermal delivery system enhances transdermal delivery rate in the early stage after application on skin and provides sustained control of the drug delivery rate in the intermediate and later stages. Thus, the drug delivery rate effective for treatment can be controlled in a sustained manner.

18 Claims, 5 Drawing Sheets

(56) References Cited

U.S. PATENT DOCUMENTS

2008/0305155 A1    12/2008    Jackson et al.
2009/0299304 A1*    12/2009    Tang ............................. 604/307
2010/0008972 A1*    1/2010    Colombo et al. ............. 424/443

OTHER PUBLICATIONS

Rubin, "New Formulation Technology of Drug," People's Publication Company, 2005, 2nd edition, pp. 568-578.

* cited by examiner

TRANSDERMAL DELIVERY SYSTEM, METHOD FOR MANUFACTURING THE SAME, AND TRANSDERMAL DELIVERY METHOD USING THE SYSTEM

CROSS-REFERENCE TO RELATED APPLICATION

The present invention claims priorities of U.S. Provisional Application No. 61/242,854 filed on Sep. 16, 2009 and Korean patent application No. 10-2009-0106090 filed on Nov. 4, 2009, which is incorporated by reference in its entirety.

FIELD

This disclosure relates to a transdermal delivery system including a plurality of adhesive layers including an intermediate adhesive layer, which contains no drug, a method for manufacturing the same, and a method for transdermal delivery using the system.

DESCRIPTION OF THE RELATED ART

The route of administration of a drug to a patient may be different depending on the particular disease or the nature of the drug. Transdermal administration is one of the administration routes. Transdermal administration may be employed to easily deliver a drug when other administration methods, e.g. oral administration, are inapplicable.

However, the transdermal delivery of a drug may be disadvantageous in terms of control of drug release rate, drug release time, or the like.

Various systems for transdermal delivery have been developed to solve this problem. For example, a microporous film is introduced between two adhesive layers to control the rate of transdermal delivery. In addition, a transdermal patch consisting of two adhesives with different delivery rates for delivering estradiol/progestin has been developed.

SUMMARY

The existing systems for transdermal delivery require a lot time to attain a desired effect since the initial rate of transdermal delivery is slow. Further, in the intermediate and later stages, the drug delivery is not continuously maintained because the drug concentration of the system decreases.

Thus, this disclosure is directed to providing a transdermal delivery system capable of improving the problems of the long time required to attain a desired effect in the early stage and the drug delivery rate decrease in the intermediate and later stages. Further, the disclosure is directed to providing a transdermal delivery system with minimized skin irritation.

In one general aspect, there is provided a transdermal delivery system including: a first adhesive layer including a drug; a drug-free second adhesive layer provided below the first adhesive layer so as to contact with the first adhesive layer and controlling a delivery rate of the drug; and a third adhesive layer provided below the second adhesive layer so as to contact with the second adhesive layer and including a drug.

In another general aspect, there is provided a method for manufacturing a transdermal delivery system, including: forming a first adhesive layer including a drug on one side of a backing layer film; forming a drug-free second adhesive layer controlling a delivery rate of the drug so as to contact with the first adhesive layer; and forming a third adhesive layer including the drug so as to contact with the second adhesive layer.

In another general aspect, there is provided a method for transdermal delivery using the transdermal delivery system.

The transdermal delivery system according to the embodiments of the disclosure provides fast skin penetration in the early stage after application and solves the problem of decreased skin penetration rate in the intermediate and later stages by continuously controlling the skin penetration rate. Further, the transdermal delivery system results in low skin irritation even after prolonged application on the skin.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In the drawings, like reference numerals in the drawings denote like elements. The shape, size and regions, and the like, of the drawing may be exaggerated for clarity.

Hereinafter, a transdermal delivery system, a method for manufacturing the same, and a method for transdermal delivery using the system according to exemplary embodiments of the disclosure will be described in detail.

As used herein, a "transdermal delivery system" refers to a system allowing delivery of a pharmacologically active drug through skin, and includes any type such as a patch.

As used herein, a "composition" included in the transdermal delivery system includes all drugs and adhesives included in a transdermal delivery system of a multi-layer structure. If a substance other than the drug and the adhesive is included, the additive is also included in the composition.

In general, a transdermal delivery system exhibits a release profile wherein a transdermal drug delivery rate is maintained until an intermediate stage while a drug concentration in an adhesive matrix is sufficiently maintained, but the delivery rate decreases as the drug concentration decreases.

In order to solve the problem of the existing transdermal delivery system, the embodiments of the disclosure provide a transdermal delivery system of a multi-layer structure, comprising a drug-free intermediate layer provided between a first adhesive layer and a third adhesive layer, each of which comprises a drug. The intermediate layer does not include the drug and may serve as a delivery rate control layer of the drug by using an adhesive different from those of the neighboring adhesive layers. The transdermal delivery system with such a structure may provide a fast drug delivery rate in the early stage as well as a continued drug delivery rate pattern with no decrease of the drug delivery rate in the intermediate and later stages.

Thus, a transdermal delivery system according to embodiments of the disclosure may comprise: a first adhesive layer comprising a drug; a drug-free second adhesive layer provided below the first adhesive layer so as to contact with the first adhesive layer and controlling a delivery rate of the drug; and a third adhesive layer provided below the second adhesive layer so as to contact with the second adhesive layer and comprising the drug.

In the transdermal delivery system according to the embodiments of the disclosure, the drug is included only in the first adhesive layer and the third adhesive layer, not in the second adhesive layer. The second adhesive layer serves to control the drug delivery rate. The second adhesive layer may comprise one or more adhesive layer(s). Further, another rate control layer may be provided at the outermost layer that directly contacts with the skin to control the rate of skin penetration.

Figure 1:
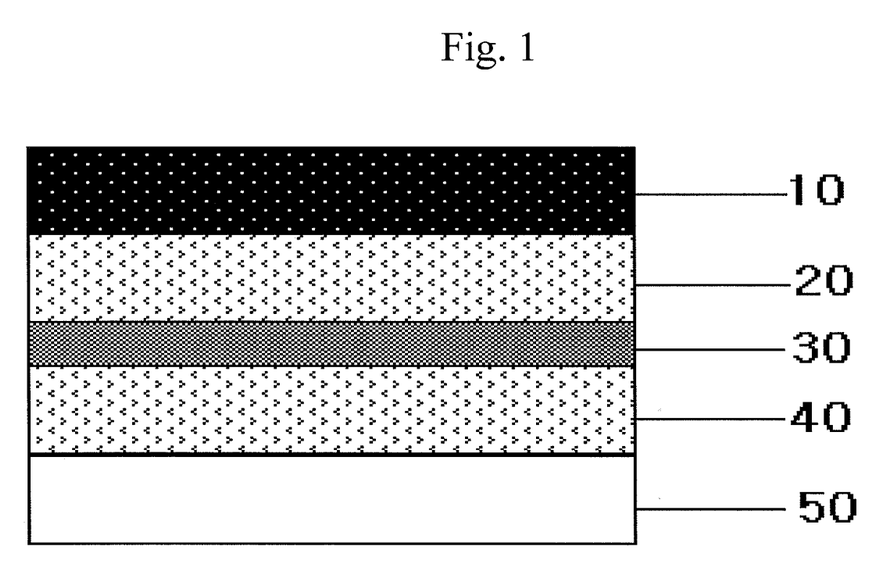
FIG. 1 is a cross-sectional view schematically illustrating a transdermal patch according to an exemplary embodiment.

FIG. 1 is a cross-sectional view schematically illustrating a transdermal patch according to an exemplary embodiment of the disclosure.

Referring to FIG. 1, a transdermal delivery system may be a multi-layer patch and may comprise, specifically, a drug-impermeable backing layer 10, a first adhesive layer 20 contacting with the backing layer 10 and comprising a drug in an amount sufficient to provide a therapeutically effective amount, a drug-free second adhesive layer 30 contacting with the first adhesive layer 20 and controlling a penetration rate of the drug, a third adhesive layer 40 contacting with the second adhesive layer 30 and also with the skin and comprising the drug in an amount sufficient to provide a therapeutically effective amount, and a removable release layer 50 contacting with the third adhesive layer 40 and being removable before application.

In the multi-layer transdermal delivery system, the third adhesive layer 40 directly contacts with the skin and allows delivery of the drug during the early stage of administration. The first adhesive layer 20 allows continued delivery of the drug from the intermediate stage. The second adhesive layer 30 contacts with the first adhesive layer 20 and may perform control such that the drug may be delivered from the first adhesive layer at a sustained rate after the early stage.

In the intermediate and later stages after application of the transdermal delivery system, the delivery of the drug decreases since the concentration of the drug in the third adhesive layer decreases gradually. This problem may be solved by providing, as in the embodiments of the disclosure, allowing the drug to be provided from the first adhesive layer to the third adhesive layer via the second adhesive layer in the intermediate and later stages. When the second adhesive layer is absent and the first adhesive layer contacts with the third adhesive layer, the drug is provided from the first adhesive layer to the third adhesive layer as soon as the drug in the third adhesive layer is depleted. In that case, the introduction of the drug from the first adhesive layer to the third adhesive layer decreases gradually in the intermediate and later stages. As a result, the initial skin penetration rate is not maintained and it is difficult to continuously deliver the drug over 24 hours.

If the second adhesive layer includes the drug, the depletion of the drug in the third adhesive layer 40 is quickly supplemented from the second adhesive layer 30 in a similar manner as when the intermediate layer is absent. As a result, the drug is quickly depleted from the transdermal delivery system and the delivery of the drug decreases rapidly in the intermediate and later stages.

In contrast, as in the embodiments of the disclosure, if the second adhesive layer 30 does not include the drug, it takes time for the drug to be supplied from the first adhesive layer 20 to the second adhesive layer 30 and then to be transferred from the second adhesive layer to the third adhesive layer 40. As a result, if the second adhesive layer does not include the drug, the second adhesive layer may function as a drug delivery rate control layer because of the time required for the drug to be transferred and the drug delivery rate may be maintained sustainedly over 24 hours by preventing the rapid decrease of the delivery rate in intermediate and later stages.

The second adhesive layer 30 is not, for example, a microporous intermediate membrane but comprises an adhesive that can dissolve the drug. When a microporous intermediate membrane incapable of dissolving the drug is used to control the skin penetration rate, the drug delivery rate is controlled only through membrane thickness, pore size, or the like. However, to transfer the drug through the pores of the microporous intermediate membrane is not efficient in terms of rate control because the pore size is very large as compared to the drug size. Further, for the drug to pass through the solid membrane which cannot dissolve the drug at all, a liquid medium capable of dissolving the drug is required. Hence, there is a limitation to apply the microporous intermediate membrane to a matrix type patch. In contrast, when an adhesive is used as the intermediate layer for rate control as in the embodiments of the disclosure, it is efficient to control the drug penetration rate because the adhesive can dissolve the drug and various interactions between the adhesive layer and the drug may be utilized depending on the characteristics and nature of the adhesive.

In the embodiments of the disclosure, the adhesives included in the first adhesive layer and the third adhesive layer may have the same or different composition.

For example, the adhesive used in the first adhesive layer and/or the third adhesive layer may be one or more adhesive(s) selected from a group consisting of an acrylate adhesive, a rubber adhesive, a silicone adhesive and an acrylate-rubber copolymer adhesive.

Although not intended to be limitative, if the drug has an amino, amide or carboxylic group, the adhesive of the first adhesive layer and/or the third adhesive layer may be an adhesive with no functional group or with a hydroxyl group, e.g. an acrylate adhesive or an acrylate-rubber copolymer adhesive.

The macromer of the acrylate-rubber copolymer may include an ethylene-butylene macromer, an ethylene-propylene macromer, an ethylene-butylene-propylene macromer, etc. The acrylate polymer of the acrylate-rubber copolymer may include those polymerized from a $C_4$-$C_{18}$ alkyl acrylate monomer, e.g., 2-ethylhexyl acrylate (2-EHA), methyl acrylate (MA) and 2-hydroethyl acrylate (2-HEA). Specific examples of the acrylate-rubber copolymer include DT87-502A, DT87-503A, DT87-504A (Henkel, Germany), etc., but are not limited thereto.

When the acrylate-rubber copolymer adhesive is used, the degree of polymerization and the weight ratio of component in said copolymer may be varied to depending on the particular drug and characteristics thereof in order to control the content and solubility of the drug in the adhesive layer, and skin penetration of the drug. For example, an increased rubber content in the copolymer adhesive results in decreased solubility of the drug in the adhesive layer and increased releasability of the drug from the transdermal system.

In the copolymer adhesive, the weight ratio (wt %) of an acrylate monomer and a rubber monomer may be from 95:5 to 10:90, specifically from 90:10 to 20:80, more specifically from 90:10 to 30:70.

The first adhesive layer and/or the third adhesive layer may further comprise microporous silica including the drug. That is to say, the drug may be encapsulated in the pores of microporous silica in order to further control the skin penetration rate. The microporous silica may be included only in the first adhesive layer or the third adhesive layer, or both in the first adhesive layer and the third adhesive layer. Silica with a smaller particle size allows inclusion of more drugs because of larger surface area. Encapsulation of the drug in the microporous silica particle results in a longer trajectory of the drug in the transdermal system, thereby reducing the release rate of the drug. This effect is more significant as the amount of the drug encapsulated in the pores of the microporous silica particle increases. Further, the employment of the microporous silica may improve stability of a drug which may become unstable due to heat or oxidation, for example, a drug having a nitrogen-containing functional group such as an amine, amide or amino group.

In the embodiments of the disclosure, the microporous silica including the drug may be uniformly dispersed in the adhesive layer. When the first adhesive layer and/or the third adhesive layer includes the microporous silica, the drug may exist only as encapsulated in the microporous silica or both as encapsulated or non-encapsulated.

As a non-limiting example, the microporous silica may be porous precipitated silica belonging to amorphous silica, having a spherical or sphere-like particle shape and having a particle size of at least 10 μm. The porous precipitated silica exists as particle or powder with good flowability even after absorbing a solvent amounting to 0.5 to 3 times its weight, and does not agglomerate.

As a non-limiting example, for uniform control of the release of the active ingredient from the silica, the silica may have a narrow particle size distribution. For example, the silica may have a particle size of 50 to 1000 μm, specifically 300 to 800 μm. The microporous silica may be included in the first adhesive layer and/or the third adhesive layer in an amount of 0.001 to 15 wt %, specifically 0.001 to 5 wt %, on the basis of weight.

In the exemplary embodiments of the disclosure, a skin penetration enhancer may be encapsulated in the microporous silica together when the drug is encapsulated. If the drug is in solid state, a skin penetration enhancer may be used as a solvent to encapsulate the drug in the pores of the silica instead of a harmful organic solvent (e.g. methanol, ethanol, acetone, DMSO, etc.). If the harmful organic solvent is used, the solvent needs to be dried after the encapsulation of the drug in the pores of the silica. During the process, a drug susceptible to heat may be degraded.

As a non-limiting example, the skin penetration enhancer may be one or more selected from a polyalcohol such as propylene glycol, an amine such as ethanolamine, a polyalcohol ester such as propylene glycol monolaurate, a surfactant, and the like.

As a non-limiting example, the drug and/or the skin penetration enhancer may be encapsulated in the pores of the silica in a short time within 1 hour through mixing or dissolving. Then, a silica composition including drug and/or the skin penetration enhancer may be directly mixed with the adhesive or by adding a polymer material such as cellulose or polyvinylpyrrolidone to the silica composition to provide viscosity and then the resulting composition may be applied on the adhesive layer.

If the microporous silica is used, the transdermal delivery system according to the embodiments of the disclosure may comprise a release retardant. The release retardant may be treated after encapsulating the drug in the pores of the silica or may be encapsulated in the pores of the silica together with the drug. If the release retardant is encapsulated in the pores of the silica together with the drug, the time required for the drug to escape from the pores of the silica increases.

The release retardant may be selected from a variety of known materials. As a non-limiting example, one or a combination of two selected from carboxymethyl cellulose, ethyl cellulose, cellulose acetate, cellulose propionate, cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(cetyl acrylate), poly(isopropyl acrylate), poly(isobutyl acrylate), poly(octadecyl acrylate), polyethylene terephthalate, hydroxyethyl cellulose, polydextrose, poly(acrylic acid), carbomer, polyvinyl alcohol, polyvinylpyrrolidone, methyl cellulose, hydroxypropyl cellulose, agar, carageenan, xanthan, hydroxypropylmethyl cellulose and polyethylene glycol may be used.

In the embodiments of the disclosure, the first adhesive layer and the third adhesive layer each may have a thickness of about 30 μm to about 300 μm, or about 30 μm to about 200 μm. If the thickness of the adhesive layer is smaller than 30

μm, it is difficult to control the thickness of the adhesive layer uniformly due to its low thinness. And, if the thickness of the adhesive layer exceeds 300 μm, the adhesive may remain on the skin after the removal of the transdermal delivery system because of cold flow.

In the embodiments of the disclosure, the first adhesive layer and the third adhesive layer may account for 10-90 wt %, specifically 30~90 wt %, of the entire transdermal delivery system. The weight proportion of the first adhesive layer and the third adhesive layer may be adjusted considering the characteristics of the drug and required skin penetration amount and pattern. For example, for an antianginal agent drug, a smoking cessation aid, an analgesic, an anesthetic or an anti-inflammatory analgesic drug requiring a fast effect, the drug may be included in a larger amount in the third adhesive layer. On the contrary, when a sustained effect is necessary such as a contraceptive or a hormone drug, the drug may be included in a larger amount in the first adhesive layer. In the embodiments of the disclosure, the weight proportion of the first adhesive layer and the third adhesive layer may be the same or different.

The drug included in the first adhesive layer and the third adhesive layer and the concentration thereof may be the same or different. In case the layers include different amount of the drug, the difference of the drug content may be not greater than 30 wt %. If the difference is greater than 30 wt %, a driving force for skin penetration is weak in the adhesive layer with the lower drug content and drug crystallization may occur in the adhesive layer with the higher drug content.

In the embodiments of the disclosure, the second adhesive layer serves as a rate control layer and comprises an adhesive but not the drug. The second adhesive layer may retard the fast transfer of the drug from the first adhesive layer to the third adhesive layer, thereby appropriately sustaining the drug delivery rate.

To provide a sustained drug delivery rate, the adhesive used in the second adhesive layer may be different from the adhesive used in the first adhesive layer and/or the third adhesive layer.

In addition, the adhesive used in the second adhesive layer may have a lower solubility for the drug than the adhesive used in the first adhesive layer and the third adhesive layer. Further, the adhesive used in the second adhesive layer may have a large difference in polarity from the adhesive used in the first adhesive layer and the third adhesive layer.

To describe in detail, if the adhesive of the second adhesive layer has a lower solubility than the adhesive of the first adhesive layer, the drug mostly remains in the first adhesive layer. As a result, the transfer rate and amount of the drug to the second adhesive layer decrease. Since the second adhesive layer has a low solubility for the drug, it includes less drug in the adhesive layer. Thus, if the second adhesive layer is provided between the first adhesive layer and the third adhesive layer, the transfer rate of the drug in the transdermal delivery system decreases because of the second adhesive layer and, hence, the transdermal penetration of the drug also is delayed. As a result, the transdermal delivery of the drug may be sustained constant even in the intermediate and later stages after application of the transdermal delivery system.

In an exemplary embodiment of the disclosure, the adhesive used in the first adhesive layer and/or the third adhesive layer may have a solubility for the drug 1.1 to 50 times, specifically 1.5 to 30 times, more specifically 1.5 to 10 times, larger than the solubility of the second adhesive layer for the drug. As the first adhesive layer and the third adhesive layer have a high solubility for the drug, crystallization is prevented and the drug may be stably included in the layers. If the solubility is less than 1.1 times, it is difficult to prevent the inflow of the drug into the second adhesive layer and to attain the desired sustained transfer of the drug. And, if the solubility exceeds 50 times, the drug may not be released from the first adhesive layer and/or the third adhesive layer. As a result, the overall skin penetration rate decreases.

In an embodiment, the number of the second adhesive layer as the rate control layer may be one or more, specifically one to three. If more than one layer is used, the drug delivery rate may be controlled more minutely. Each rate control layer may include the same or different adhesive. Similar adhesives having the same or similar solubility for the drug and polarity may be used.

The adhesive of the rate control layer may be selected considering the adhesive of the first adhesive layer and/or the third adhesive layer, the drug involved and its characteristics. As a non-limiting example, one or more selected form an acrylate adhesive, a rubber adhesive and a silicone adhesive may be used. Although not intended to be limitative, a silicone or rubber adhesive may be used when the drug has an amino, amide or carboxylic group.

The silicone adhesive used as the adhesive of the rate control layer may be an adhesive comprising a monomer having a methyl group substituted at silicon, a monomer having a phenyl group substituted at silicon, or a mixture thereof. Examples include Bio-PSA 7-4101, Bio-PSA 7-4102, Bio-PSA 7-4201, Bio-PSA 7-4202, Bio-PSA 7-4301, Bio-PSA 7-4302, Bio-PSA 7-4501, Bio-PSA 7-4601 (Dow Corning), etc.

And, examples of the acrylate adhesive may include DT87-2196, DT87-2510, DT87-2677, DT87-2852, DT87-4098, DT87-9301, DT87-202A, DT87-208A, DT87-235A (Henkel, Germany), etc.

And, examples of the rubber adhesive may include DT87-608A, DT87-611A, etc. Further, a mixture of high-molecular-weight polyisobutylene (PIB) having a molecular weight of about 500,000 to 1,500,000 daltons and a low-molecular weight PIB having a molecular weight of about 100 to 10,000 daltons may be used.

In addition, one or more another rate-control adhesive layer(s) which may not contact with the second adhesive layer may be provided. For example, it may be provided outside the third adhesive layer.

The second adhesive layer may have a thickness of 5 to 200 μm, specifically 5 to 100 μm. If the thickness is smaller than 5 μm, it is difficult to control the thickness of the adhesive layer uniformly due to its low thinness. And, if the thickness of the adhesive layer exceeds 100 μm, the adhesive may remain on the skin after the removal of the transdermal delivery system (cold flow) or separation may occur in the adhesive matrix layer (adhesive failure). Further, the drug penetration rate may be overly decreased.

The second adhesive layer may account for 1 to 70 wt %, specifically 1 to 60 wt %, of the total weight of the disclosure transdermal delivery system.

In the embodiments of the disclosure, for example, the first adhesive layer/the second adhesive layer/the third adhesive layer may be configured as a rubber adhesive/an acrylate adhesive/a rubber adhesive (hereinafter, referred to as R/A/R). However, this is not recommended because when the acrylate adhesive having the largest solubility is used in the drug-free second adhesive layer, inflow of the drug from the first adhesive layer to the second adhesive layer is not controlled adequately.

In another exemplary embodiment, the first adhesive layer/the second adhesive layer/the third adhesive layer may be configured as a silicone adhesive/an acrylate adhesive/a silicone adhesive (hereinafter, referred to as S/A/S). This may also be inadequate for sustained delivery of the drug since the acrylate adhesive having large solubility is provided in the intermediate layer. Further, the use of the silicone adhesive in the first adhesive layer and the third adhesive layer may be inadequate since a long time is required to attain the medicinal effect.

In the second adhesive layer, an adhesive with a low solubility for the drug, such as a rubber adhesive, e.g. polyisobutylene, or a silicone adhesive may be used, in order to achieve sustained delivery of the drug.

For example, the first adhesive layer/the second adhesive layer/the third adhesive layer may be configured as an acrylate adhesive/a rubber adhesive (e.g. polyisobutylene)/an acrylate adhesive (hereinafter, referred to as A/R/A). Since the drug in the acrylate adhesive layer as the first adhesive layer having a larger solubility for the drug is transferred very slowly to the rubber adhesive layer having a lower solubility for the drug, the drug can be delivered in a sustained manner. In addition, a configuration of an acrylate adhesive (A) or an acrylate-rubber blend (or copolymer) adhesive (A+R)/a silicone adhesive (S)/an acrylate adhesive or an acrylate-rubber blend (or copolymer) adhesive (hereinafter, referred to as A or A+R/S/A or A+R) may be employed. In this case, the transfer of the drug from the first adhesive layer to the intermediate, second adhesive layer may be controlled adequately through the difference in solubility for the drug of the neighboring copolymer adhesive and silicone adhesive. Further, if the silicone adhesive is included in the intermediate layer, a faster skin penetration rate in the early stage and a sustained skin penetration rate of the drug in the intermediate and later stages may be attained more easily than when a silicone adhesive layer is provided outside the third adhesive layer.

According to the disclosure, there is provided a transdermal delivery system wherein an adhesive capable of minimizing skin irritation is provided in the adhesive layer that directly contacts with the skin, in order to minimize skin irritation.

Hereinafter, a method for manufacturing the transdermal delivery system according to the embodiments of the disclosure will be described.

Specifically, the method may include: forming a first adhesive layer comprising a drug on one side of a backing layer film; forming a drug-free second adhesive layer controlling a delivery rate of the drug so as to contact with the first adhesive layer; and forming a third adhesive layer comprising the drug so as to contact with the second adhesive layer.

The first adhesive layer may be coated on a backing layer film made of a nonwoven, a polyester film or a polyurethane film impermeable to light or the drug component. Subsequently, after drying (e.g. by hot air drying at 50 to 120° C.), a rate-control adhesive layer may be formed thereon.

The rate-control adhesive layer may be formed by coating a drug-free second adhesive on a release film and then drying (e.g. by hot air drying at 50 to 120° C.). After the second adhesive layer is formed on the first adhesive layer, the release film attached to the second adhesive layer is removed.

Subsequently, a previously prepared third adhesive layer is formed on the second adhesive layer. The third adhesive layer may be formed by coating a drug-containing third adhesive on a release liner and then drying (e.g. by hot air drying at 50 to 120° C.).

In the embodiments of the disclosure, a pharmacologically active drug may be a central nervous system drug, an anti-inflammatory analgesic, an antidepressant, a circulatory system drug, a bronchial drug, a smoking cessation aid, a hair restorer, a whitening agent, an antidementia agent, an antispasmodic, an antianginal agent, a urinary system drug, or the like. The drug may account for 1 to 50 wt %, specifically 5 to 40 wt %, of the total weight of the transdermal delivery system. The drug may be included in the adhesive layer by adding the drug to the adhesive and then coating the adhesive.

As non-limiting examples, the central nervous system drug may be an antidepressant, an antidementia agent treating dementia caused by Alzheimer's disease or Parkinson's disease, a drug for treating attention-deficit hyperactivity disorder (ADHD), epilepsy, or the like.

As non-limiting examples, the antidepressant drug may be selegiline, the antidementia drug may be donepezil, rivastigmine, rotigotine, ropinirole, etc., the ADHD drug may be methylphenidate, and the epilepsy drug may be topiramate, divalproex, lamotrigine, levetiracetam, sumatriptan, etc.

As non-limiting examples, the antianginal agent drug may be nitroglycerin, the analgesic may be fentanyl, buprenorphine, lidocaine or capsaicin, the bronchial drug may be tulobuterol or clenbuterol, the hair restorer may be finasteride or dutasteride, the smoking cessation aid may be nicotine or a derivative thereof, and the whitening agent may be hydroquinone, adapalene, alpha-lipoic acid, etc.

Although not intended to be limitative, the drug used in the embodiments of the disclosure may be a drug having a small molecular weight, e.g. 500 g/mol or smaller, or a drug having a relatively high initial skin penetration rate.

Also, in the embodiments of the disclosure, a drug with a higher solubility in an acrylate adhesive than in a silicone adhesive (So are most of the aforementioned drugs) may be used.

Further, in the embodiments of the disclosure, the drug may be selected from one having a relatively high skin penetration rate in the early stage. Specifically, a drug showing a relatively high skin penetration rate in the early stage but the rapid skin penetration rate decreases in the intermediate and later stages as the drug concentration in the transdermal matrix decreases may be selected.

Non-limiting examples of the pharmacologically active drug may include nicotine, nitroglycerin, tulobuterol, clenbuterol, fentanyl, buprenorphine, capsaicin, donepezil, rotigotine, selegiline, finasteride, dutasteride, methylphenidate, rivastigmine, etc.

The drug may also be in salt or base form. A base form may be favorable in terms of skin penetration, but the disclosure is not particularly limited thereto.

In the embodiments of the disclosure, the drug may be a drug containing nitrogen having, for example, an amino or amide group. The drug may be unstable against oxygen or moisture in the air, light, heat, or the like. Thus, the transdermal delivery system according to the disclosure may optionally comprise a preservative, an antioxidant, an anti-browning agent, a filler, or the like either alone or in combination. These materials may be natural or synthetic ones.

As non-limiting examples, commonly known antioxidants or derivatives thereof may be used as a synthetic antioxidant. For example, butylated hydroxytoluene, butylated hydroxyanisole, ascorbic acid, alpha-lipoic acid, cinnamic acid, gallic acid, propyl gallate, glycerin, propylene glycol, hydroquinone, citric acid, melanoidin, sulfites such as sulfurous anhydride, sodium sulfite or sodium hyposulfite, chlorites such as sodium hypochlorite, 1-sorbic acid, sodium 1-sorbate, or the like may be used alone or in combination.

As non-limiting examples, one or more selected from alpha-tocopherol and its derivatives, vitamin C, herb extract, catechin, polyphenol, flavonoid, etc. may be used as a natural antioxidant.

As a non-limiting example, the preservative may be one or more selected from dehydroacetic acid, potassium sorbate, calcium sorbate, sodium benzoate, potassium benzoate, calcium benzoate, methyl p-oxybenzoate, propyl p-oxybenzoate, sodium propionate and calcium propionate.

In the exemplary embodiments of the disclosure, although not intended to be limitative, when a nitrogen-containing drug such as rivastigmine, selegiline, donepezil, nicotine, etc. is used in a free base form, one or more of a preservative, an antioxidant, an anti-browning agent and a filler may be added thereto.

The transdermal delivery system according to the embodiments of the disclosure may comprise 0.01 to 20 wt % of a skin penetration enhancer in the first adhesive layer and/or the third adhesive layer. The skin penetration enhancer may be selected from various known materials without particular limitation. As a non-limiting example, natural and synthetic fats, oils and waxes, fatty acids, fatty acid esters, polyhydroxy fatty acid esters, polyhydroxy fatty acids, fatty alcohols, fatty alcohol ethoxylates, essential oils, vegetable oils and their derivatives, sterols and sterol derivatives, polyolefins, emulsions, emollients, humectants, cosmetically acceptable topical ingredients, or the like may be used. Specifically, glycerin, propylene glycol or mono- or diester of propylene glycol may be used.

Further, in the embodiments of the disclosure, transdermal administration may be performed using the transdermal delivery system. For example, the transdermal delivery system may be attached on the skin of human or animal to carry out transdermal delivery.

The examples and experiments will now be described. The following examples and experiments are for illustrative purposes only and not intended to limit the scope of this disclosure.

Example 1

In order to prepare the first adhesive layer and the third adhesive layer, an acrylate adhesive DT87-502A (Henkel) was mixed with rivastigmine, and then propylene glycol monolaurate (PGML) was added thereto and mixed well.

The resulting composition was divided in equal amount and coated respectively on a backing layer (Scotchpak 1109 polyester film, 3M) and a liner (Scotchpak 9744, 1022, paper release liner 1361, 9743, 3M) using a Lab coater and dryer (Mathis, Switzerland) and hot air dried at 75° C. to prepare the first adhesive layer and the third adhesive layer.

A silicone adhesive PSA 7-4501 (Dow Corning) was coated on a fluoropolymer-coated release liner (Scotchpak 9748, 3M) and hot air dried at 75° C. to prepare the rate-control adhesive layer.

After laminating the rate-control adhesive layer on the first adhesive layer as an intermediate adhesive layer, the third adhesive layer was laminated thereon. Thus manufactured patch had a composition as described in Table 1. The size was 1.6×1.6 cm$^2$.

TABLE 1

| Ingredients | Contents (wt %) |
|---|---|
| Acrylate adhesive DT87-502 | 67% |
| Rivastigmine | 16% |
| PGML | 2% |
| Silicone adhesive PSA 7-4501 | 15% |

Comparative Example 1

A transdermal patch without a rate-control adhesive layer was manufactured.

An acrylate adhesive DT87-502A (Henkel, Germany) was mixed with rivastigmine, and then PGML was added thereto and mixed well. The resulting composition was divided in equal amount and coated respectively on a backing layer (Scotchpak 1109 polyester film, 3M) and a liner (Scotchpak 9744, 1022, paper release liner 1361, 9743, 3M) using a Lab coater and dryer (Mathis, Switzerland) and hot air dried at 75° C. to prepare the first adhesive layer and the third adhesive layer. Thus manufactured patch had a composition as described in Table 2. The size was 2.0×2.0 cm$^2$.

TABLE 2

| Ingredients | Contents (wt %) |
|---|---|
| Acrylate adhesive DT 87-502 | 82% |
| Rivastigmine | 16% |
| PGML | 2% |

The patches manufactured in Example 1 and Comparative Example 1 included the drug at a concentration of 18.1 mg/10 cm$^2$.

[Pharmacokinetic Test in Animal]

The patches manufactured in Example 1 and Comparative Example 1 were tested at least 2 weeks after the manufacture. For test animals, 6-week-old hairless rats purchased from SLC (Japan) weighing about 230 g were used after an accommodation period of about a week. The patches of Example 1 and Comparative Example 1 and a commercially available patch Exelon® were attached to 6 rats, respectively. Blood concentration of the drug was measured twice as shown in Table 3.

Figure 2:
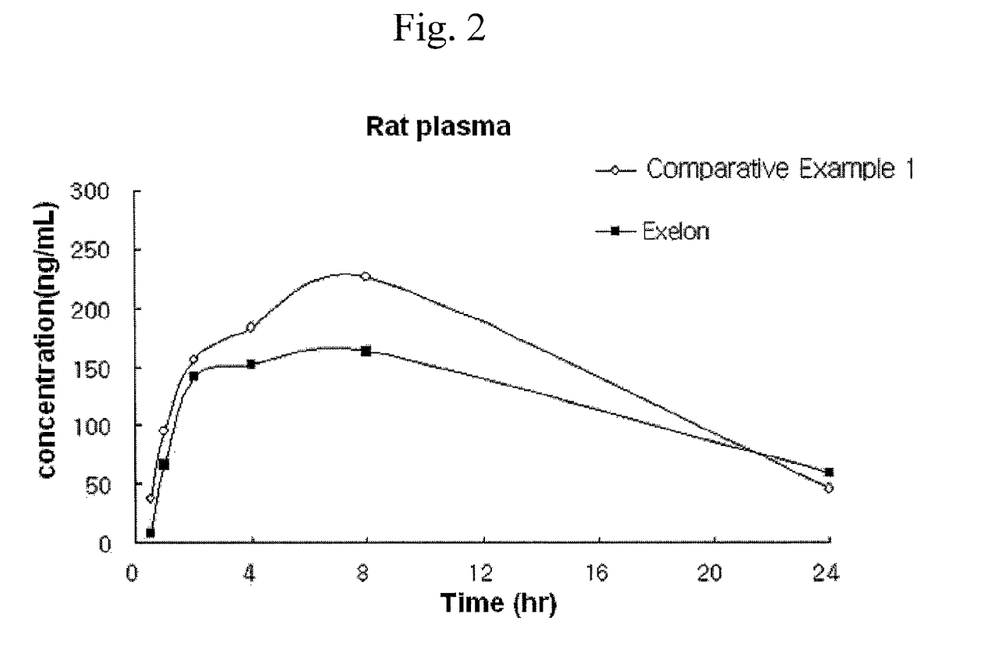
FIG. 2 is a graph comparing blood concentration for Comparative Example 1 and a commercially available product [In FIG. 2, the X-axis is time (hr) and the Y-axis is concentration (ng/mL)]
Figure 3:
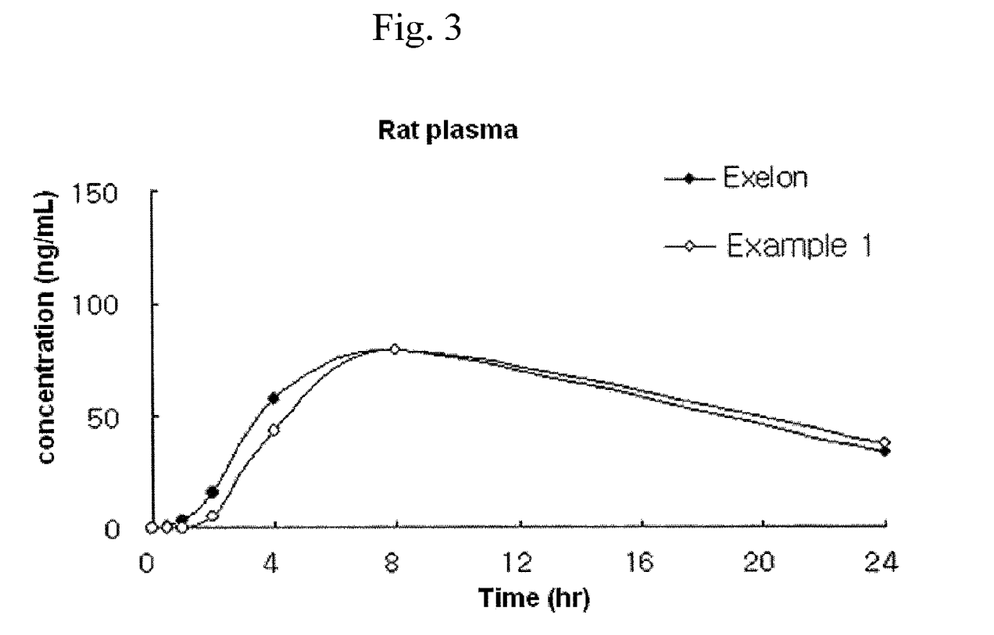
FIG. 3 is a graph comparing blood concentration for Example 1 and a commercially available product [In FIG. 3, the X-axis is time (hr) and the Y-axis is concentration (ng/mL)]

Blood was taken from each rat 6 times over 24 hours and analyzed according to a method reported in the literature (*Journal of Chromatography B*, 784 (2003) 301-304). The result is given in Tables 4 and 5. The blood concentration is shown in FIGS. 2 and 3.

TABLE 3

| | Comparative Example 1 (Negative Control) | Positive Control 1 | Example 1 | Positive Control 2 |
|---|---|---|---|---|
| Patch type | Comparative Example 1 | Commercially available patch Exelon ® | Example 1 | Commercially available patch Exelon ® |
| Patch size (cm$^2$) | 2.0 × 2.0 | 2.0 × 2.0 | 1.6 × 1.6 | 1.6 × 1.6 |
| Drug content (mg/10 cm$^2$) | 18.1 | 18.1 | 18.1 | 18.1 |

TABLE 4

Pharmacokinetic test result for Comparative Example 1

| | Comp. Ex. 1 | Positive Control 1 | Comparison |
|---|---|---|---|
| Terminal half life (hr) | 7.1 | 11.3 | 63% of commercially available patch |

TABLE 5

Pharmacokinetic test result for Example 1

|  | Ex. 1 | Positive Control 2 | Comparison |
|---|---|---|---|
| Terminal half life (hr) | 15.28 | 12.79 | 120% of commercially available patch |

As seen from FIG. 2, the patch of Comparative Example 1 resulted in a shorter terminal hale life as compared to Positive Control 1 because the drug delivery rate was not continuously maintained in the intermediate and later stages. In contrast, as seen from FIG. 3, the patch of Example 1 showed a sustained drug delivery rate in the intermediate and later stages as compared to Positive Control 2, as well as a superior terminal hale life. To conclude, the patch of Example 1 exhibited better drug delivery in the intermediate and later stages than the patch of Comparative Example 1 and Exelon®.

[Skin Penetration Test]

In vitro skin penetration of the patch of Example 1 was compared with the Exelon® patch of Positive Control 2. The commonly employed Franz diffusion cell (Hwa-in co, Korea) and human cadaver skin (1-3 mm thick, Han's Bio, Korea) were used for the skin penetration test. Human cadaver skin (3 cm$^2$) was loaded in the Franz diffusion cell and the test material cut into a circular disc of a 1.5 cm diameter was attached on the skin. Test temperature was set at 32° C. Phosphate buffer (pH 7) was used as the receptor solution. The content of rivastigmine in the receptor solution was quantitatively analyzed by HPLC.

TABLE 6

|  | Skin penetration amount (μg/mL) | |
|---|---|---|
| Time (hour) | Example 1 | Positive Control 2 |
| 0 | 0.0 | 0.0 |
| 1 | 60.3 | 47.2 |
| 2 | 189.1 | 137.7 |
| 4 | 413.4 | 305.7 |
| 8 | 815.9 | 613.3 |
| 24 | 1745.3 | 1279.2 |
| Js (μg/cm$^2$ · hr) | 64.2 | 46.7 |
| Relative accumulated skin penetration | 1.36 | 1.00 |

Figure 4:
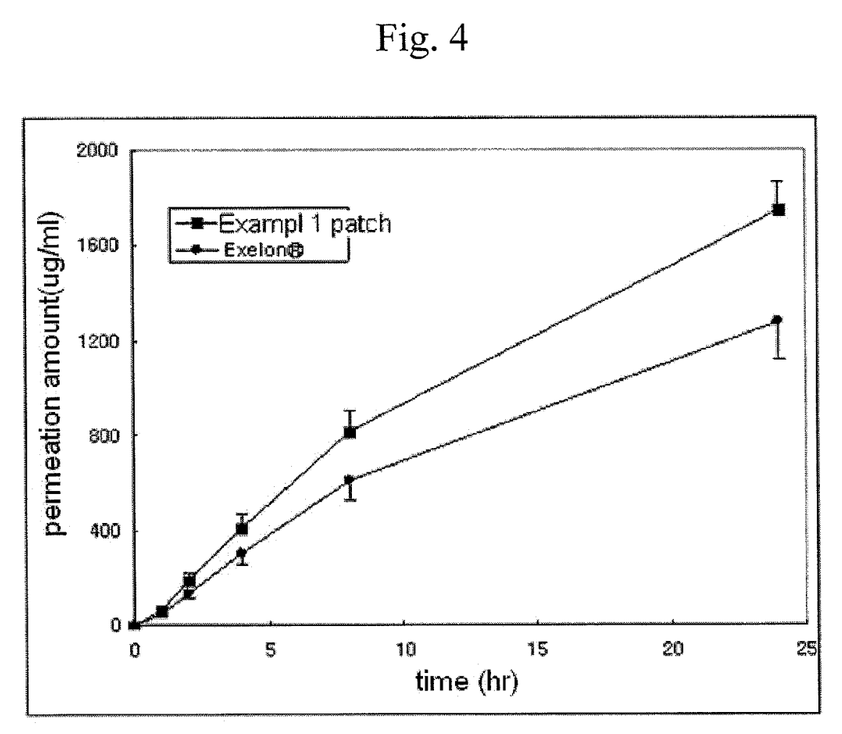
FIG. 4 is a graph comparing in vitro skin penetration for Example 1 and a commercially available product [In FIG. 4, the X-axis is time (hr) and the Y-axis is permeated drug ($\mu g/cm^2$)]

As seen from Table 6 and FIG. 4, Example 1 exhibited faster skin penetration in the early stage as well as larger skin penetration amount when compared with Positive Control 2.

[Skin Irritation Test]

Skin irritation was compared for the patches of Example 1 and Positive Control 2 (size: 2.5 cm×2.5 cm). Gauze soaked with sterilized physiological saline was used as the control material. Each group consisted of 3 male New Zealand white rabbits (body weight: 3.1-3.7 kg). The back of the rabbit was depilated 24 hours before applying the patches. On the test day, remaining fine hairs were removed and the patches were attached on the right and left side around the neck and back, two on the intact skin and two on the abraded skin. After covering a impermeable thin solid paper with no reactivity, the patch was covered and protected with a film (Tegarderm™, 3M Health Care, USA) and an elastic bandage (Coban™, width: 6.4 cm, 3M Health Care, USA).

Skin irritation and response were investigated according to 'Text-Table 1. Erythema & Eschar and 'Text-Table 2. Edema formation' of the "Guideline for Toxicity Test of Medical and Other Products (KFDA Notification 1999-61, Dec. 22, 1999)". At 24 and 72 hours after the application of the patches, skin response score was recorded. After summing the Erythema & Eschar and Edema scores and edema formation scores and averaging, the primary irritation index (PII) was calculated. Then, the degree of irritation was classified according to 'Text-Table 3. Classification of skin irritation'. The result is given in Table 7.

TABLE 7

| Test materials | Primary irritation index (PII) | Skin irritation extent |
|---|---|---|
| Example 1 | 0.165 | No Irritation |
| Positive Control 2 | 1.5 | Mild Irritation |

The patch of Example 1 was No Irritation (PII=0.165) with no skin irritation, whereas the patch of Positive Control 2 was Mild Irritation (PII=1.5). Thus, Example 1 according to the disclosure was superior in skin irritation than the commercially available product.

Example 2

A patch was manufactured by further adding microporous silica and a release control agent.

Example 2-1

A patch was manufactured in a manner similar to Example 1 as the composition shown in Table 8, by further adding propylene glycol (PG) when mixing with PGML.

Example 2-2

As seen in Table 8, rivastigmine was mixed with PGML and propylene glycol. After the mixture was dissolved, was slowly added to Tixosil® silica while mixing with hands so that the solution was absorbed in the microporous silica. The resulting silica composition was mixed with DT87-502A (Henkel) as in Example 1. Then, a patch was manufactured in the same manner as Example 1.

Example 2-3

A patch was manufactured in the same manner as Example 2-2, except that, as seen in Table 8, polyvinylpyrrolidone (PVP; PVP90F, BASF) was mixed with rivastigmine, PG and PGML, was slowly added to silica while mixing with hands so that the solution was absorbed in the microporous silica.

TABLE 8

|  | Contents (wt %) | | |
|---|---|---|---|
| Ingredients | Ex. 2-1 | Ex. 2-2 | Ex. 2-3 |
| DT87-502 | 63% | 61% | 61% |
| Rivastigmine | 16% | 16% | 16% |
| PGML | 1% | 1% | 1% |
| PG | 5% | 5% | 5% |
| PSA 7-4501 | 15% | 15% | 15% |
| Silica | — | 2% | 1.99% |
| PVP90F | — | — | 0.01% |

[Skin Penetration Test]

Figure 5:
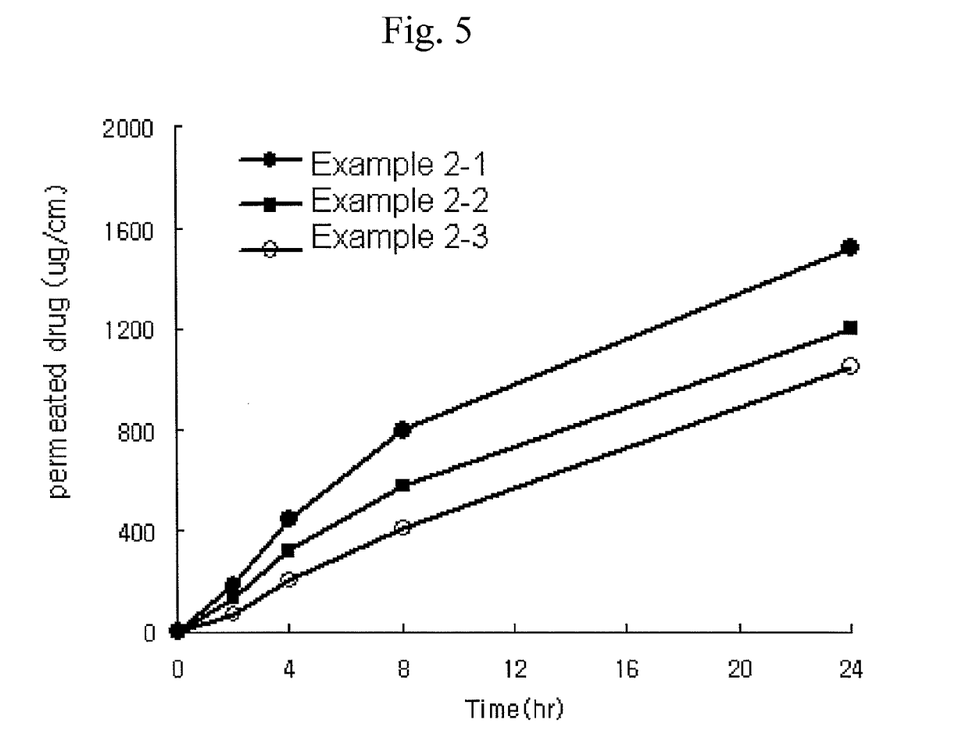
FIG. 5 is a graph showing a skin penetration test result of Example 2 [In FIG. 5, the X-axis is time (hr) and the Y-axis is permeated drug ($\mu g/cm^2$)].

Skin penetration test was carried out for the patch of Example 2 using the Franz diffusion cell and human cadaver skin. The result is shown in FIG. 5.

Example 2-2, wherein silica was introduced, exhibited 21.03% or more delayed skin penetration as compared to Example 2-1. And, Example 2-3, wherein the release control agent was introduced, exhibited 12.95% or more delayed skin penetration as compared to Example 2-2.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A transdermal delivery system comprising:
a first adhesive layer comprising a drug;
a drug-free second adhesive layer provided below the first adhesive layer so as to contact with the first adhesive layer and controlling a delivery rate of the drug; and
a third adhesive layer provided below the second adhesive layer so as to contact with the second adhesive layer and comprising the drug,
wherein the drug-free second adhesive layer is in contact with the first adhesive layer on its one surface and is in contact with the third adhesive layer on the opposite surface, and wherein the first adhesive layer and the third adhesive layer each have a solubility for the drug 1.1 to 50 times larger than the solubility of the second adhesive layer for the drug.

2. The transdermal delivery system according to claim 1, wherein an adhesive of the first adhesive layer is the same as or different from that of the third adhesive layer.

3. The transdermal delivery system according to claim 2, wherein the adhesive of the first adhesive layer is the same as that of the third adhesive layer.

4. The transdermal delivery system according to claim 1, wherein an adhesive of the first adhesive layer or the third adhesive layer is one or more selected from a group consisting of an acrylate adhesive, a rubber adhesive, a silicone adhesive and an acrylate-rubber copolymer adhesive.

5. The transdermal delivery system according to claim 4, wherein the adhesive of the first adhesive layer or the third adhesive layer is an acrylate adhesive or an acrylate-rubber copolymer adhesive.

6. The transdermal delivery system according to claim 5, wherein the acrylate-rubber copolymer adhesive comprises an acrylate monomer and a rubber monomer at 95:5 to 10:90 based on weight.

7. The transdermal delivery system according to claim 1, wherein an adhesive of the second adhesive layer is one or more selected from a group consisting of an acrylate adhesive, a rubber adhesive and a silicone adhesive.

8. The transdermal delivery system according to claim 7, wherein the adhesive of the second adhesive layer is a rubber adhesive or a silicone adhesive.

9. The transdermal delivery system according to claim 1, wherein the first adhesive layer/the second adhesive layer/the third adhesive layer are an acrylate adhesive/a rubber adhesive/an acrylate adhesive; or an acrylate adhesive, or an acrylate-rubber blend or copolymer adhesive/a silicone adhesive/ an acrylate adhesive or an acrylate-rubber blend or copolymer adhesive.

10. The transdermal delivery system according to claim 1, wherein one or more of the first adhesive layer and the third adhesive layer further comprises microporous silica including the drug.

11. The transdermal delivery system according to claim 10, wherein the microporous silica is comprised in an amount of 0.001 to 15 wt % in one or more of the first adhesive layer and the third adhesive layer.

12. The transdermal delivery system according to claim 1, wherein the drug is a central nervous system drug, an anti-inflammatory analgesic, an antidepressant, a circulatory system drug, a bronchial drug, a smoking cessation aid, a hair restorer, a whitening agent, an antidementia agent, an antispasmodic, an antianginal agent or a urinary system drug and is comprised in an amount of 1 to 50 wt % based on the total weight of the composition included in the transdermal delivery system.

13. The transdermal delivery system according to claim 12 wherein the drug is one or more selected from a group consisting of nicotine, nitroglycerin, tulobuterol, clenbuterol, fentanyl, buprenorphine, capsaicin, donepezil, rotigotine, selegiline, finasteride, dutasteride, methylphenidate and rivastigmine.

14. The transdermal delivery system according to claim 1, wherein one or more of the first adhesive layer and the third adhesive layer comprises 0.01 to 20 wt % of a skin penetration enhancer.

15. The transdermal delivery system according to claim 1, wherein the second adhesive layer accounts for 1 to 70 wt % of the transdermal delivery system.

16. A transdermal delivery system which is a multi-layer patch comprising:
a drug-impermeable backing layer (10);
a first adhesive layer (20) contacting with the backing layer (10) and comprising a drug in an amount sufficient to provide a therapeutically effective amount;
a drug-free second adhesive layer (30) contacting with the first adhesive layer (20) and controlling a penetration rate of the drug;
a third adhesive layer (40) contacting with the second adhesive layer (30) and also with the skin, and comprising the drug in an amount sufficient to provide a therapeutically effective amount; and
a removable release layer (50) contacting with the third adhesive layer (40) and being removable before application,
wherein the drug-free second adhesive layer is in contact with the first adhesive layer on its one surface and is in contact with the third adhesive layer on the opposite surface, and wherein the first adhesive layer and the third adhesive layer each have a solubility for the drug 1.1 to 50 times larger than the solubility of the second adhesive layer for the drug.

17. A method for transdermal delivery comprising applying the transdermal delivery system according to claim 1 any one of claims 1 or 2-16.

18. A method for manufacturing a transdermal delivery system, comprising:
forming a first adhesive layer comprising a drug on one side of a backing layer film;
forming a drug-free second adhesive layer controlling a delivery rate of the drug so as to contact with the first adhesive layer; and
forming a third adhesive layer comprising the drug so as to contact with the second adhesive layer,
wherein the drug-free second adhesive layer is in contact with the first adhesive layer on its one surface and is in contact with the third adhesive layer on the opposite surface, and wherein the first adhesive layer and the third adhesive layer each have a solubility for the drug 1.1 to 50 times larger than the solubility of the second adhesive layer for the drug.

* * * * *